United States Patent [19]

Wilk et al.

[11] Patent Number: 5,398,685
[45] Date of Patent: Mar. 21, 1995

[54] ENDOSCOPIC DIAGNOSTIC SYSTEM AND ASSOCIATED METHOD

[76] Inventors: Peter J. Wilk, 185 W. End Ave., New York, N.Y. 10023; Naomi L. Nakao, 303 E. 57th St., New York, N.Y. 10022

[21] Appl. No.: 904,862

[22] Filed: Jun. 26, 1992

Related U.S. Application Data

[63] Continuation-in-part of Ser. No. 819,120, Jan. 10, 1992.

[51] Int. Cl.⁶ ............................ A61B 5/00; A61B 1/06; A61B 8/00
[52] U.S. Cl. ......................... 128/653.1; 128/662.06; 128/664; 128/665; 128/4; 128/6; 348/65; 348/68; 364/413.13; 364/413.25; 382/6
[58] Field of Search ............... 128/4, 6, 662.06, 653.1, 128/664, 665; 358/98; 382/6; 348/65, 67–68; 364/413.13, 413.25

[56] References Cited

U.S. PATENT DOCUMENTS

| | | | |
|---|---|---|---|
| 4,868,645 | 9/1989 | Kobayashi | 128/6 |
| 4,932,412 | 6/1990 | Goldenberg | 128/654 |
| 4,981,138 | 1/1991 | Deckelbaum et al. | 128/665 |
| 4,998,282 | 3/1991 | Shishido et al. | 128/4 |
| 5,003,979 | 4/1991 | Merickel et al. | 128/653.2 |
| 5,005,559 | 4/1991 | Blanco et al. | 128/4 |
| 5,050,607 | 9/1991 | Bradley et al. | 128/653.1 |
| 5,121,750 | 6/1992 | Katims | 128/662.06 |
| 5,188,111 | 2/1993 | Yates et al. | 128/662.06 |
| 5,211,167 | 5/1993 | Amenomori | 128/662.06 |
| 5,261,404 | 11/1993 | Mick et al. | 128/653.1 |

*Primary Examiner*—Krista M. Pfaffle
*Attorney, Agent, or Firm*—R. Neil Sudol; Henry D. Coleman

[57] ABSTRACT

A method for use in medical diagnosis uses an endoscope having an insertion member, a sensor mounted at least in part to the insertion member for receiving energy waves from internal body tissues of a patient, and a converter operatively connected to the sensor for generating electrical signals encoding information contained in the energy waves. An analyzing unit is operatively connected to the converter for automatically identifying an organic object from the electrically encoded information, while a signal generator is operatively connected to the analyzing unit for automatically generating an alert signal sensible by an operator to inform the operator of the existence of the organic object.

9 Claims, 3 Drawing Sheets

ENDOSCOPIC DIAGNOSTIC SYSTEM AND ASSOCIATED METHOD

CROSS-REFERENCE TO RELATED APPLICATION

This application is a continuation-in-part of U.S. Ser. No. 819,120, filed Jan. 10, 1992.

BACKGROUND OF THE INVENTION

This invention relates to an automated system for use in making medical diagnoses. More particularly, this invention relates to an automated endoscopic system for providing assistance to an endoscopist in making diagnostic determinations and, more specifically, in identifying such internal organic objects as polyps.

In making an endoscopic examination, a doctor or other user inserts an endoscope into a patient while viewing images internal organic structures at the distal end of the endoscope insertion member. The images may be presented via an eyepiece or on a video monitor. In any event, it is not unusual for small polyps and other organic objects of interest to be missed by the endoscopist during the endoscopic examination. Frequently, a small polyp is partially obscured by another polyp or another internal structure. In addition, on occasion the passage of the endoscope insertion member through an intestine may be inadvertantly too quick for a complete and thorough examination of the intestinal wall. Moreover, an inexperienced endoscopist may somtimes overlook a structural iregularity which a more experienced observer would not fail to notice.

The dangers of overlooking a polyp during an endoscopic examination are clear. A small polyp which is missed may be malignant whereas a larger polyp, which is observed, may be benign.

OBJECTS OF THE INVENTION

An object of the present invention is to provide a method and/or a device or system for assisting the endoscopist in detecting the presence of polyps and other internal organic structures during an endoscopic examination.

Another object of the present invention is to provide such a method and/or device or system which is at least partially automated.

Other objects of the present invention will be apparent from the detailed descriptions and drawings included herein.

SUMMARY OF THE INVENTION

A system for use in medical diagnosis comprises, in accordance with the present invention, an endoscope having an insertion member, a sensor assembly mounted at least in part to the insertion member for receiving energy waves from internal body tissues of a patient and for generating electrical signals encoding information contained in the energy waves, an analyzing unit operatively connected to the sensor assembly for automatically identifying an organic object from the electrically encoded information, and a signal generator operatively connected to the analyzing unit for automatically generating an alert signal sensible by an operator to inform the operator of the existence of the organic object.

Pursuant to alternative or mutually complementary features of the present invention, the sensor assembly includes an ultrasonic detector, an optical radiation detector such as a charge coupled device, and/or an infrared radiation detector.

According to another feature of the present invention, the system further comprises a video monitor and circuitry operatively connected to the video monitor and the converter for generating a visual image containing the information. The signal generator then includes means operatively connected to the video monitor for providing a visual indication of the organic object upon identification thereof by the analyzing unit. Specifically, circuitry or programming may be provided for highlighting an image of the organic object on the monitor, for example, by generating a circle surrounding the image of the organic object on the monitor. Alternatively or additionally, circuitry or programming may be provided for freezing an image on the monitor upon identification of the object by the analyzing unit.

As yet another alternative or addition, the signal generator may include an electroacoustic transducer for producing an audible signal.

In accordance with another conceptualization of the present invention, a system for use in medical diagnosis comprises an endoscope having an insertion member, a sensor assembly mounted at least in part to the insertion member for receiving energy waves from internal body tissues of a patient and for digitizing data from the energy waves as to internal organic structures of the patient, a memory for storing medical data for a multiplicity of previously identified internal organic structures, and a computer or microprocessor operatively connected to the memory and the sensor assembly for comparing digitized data about the patient's internal tissues with the data stored in the memory means and for identifying a predetermined type of organic structure. An output component is operatively connected to the computing means for communicating the identification to a user.

Pursuant to another feature of the present invention, the output component includes a signal generator operatively connected to the computer for automatically generating an alert signal sensible by an operator to inform the operator of the existence of the an identified organic object of the predetermined type.

According to a further feature of the present invention, the sensor assembly includes a scanner for generating in electrically encoded form an image of a visually perceptible organic part of the patient.

A medical diagnostic method comprises, in accordance with the present invention, the steps of (a) inserting into a patient an insertion member of an endoscope, (b) operating the endoscope to receive energy waves from internal body tissues of the patient proximate to a distal end of the insertion member, (c) automatically digitizing data from the energy waves as to internal organic structures of the patient, (d) automatically analyzing the digitized data, (e) during the step of analyzing, automatically identifying an organic object from the digitized data, and (f) automatically generating an alert signal sensible by an operator to inform the operator of the existence of the organic object.

Pursuant to another feature of the present invention, the step of sensing includes the step of detecting incoming optical radiation, infrared radiation and/or ultrasonic pressure waves.

Where a visual image containing the information is generated, for example, on a video monitor, the alert signal includes a visual indication of the organic object upon identification thereof. The method may comprise more specifically the step of highlighting an image of the organic object on the monitor, for example, by generating a circle surrounding the image of the organic object on the monitor.

The step of generating an alert signal may additionally or alternatively include the step of producing an audible signal.

According to another feature of the present invention, automatically analyzing the digitized information includes the steps of (i) storing medical data for a multiplicity of previously identified internal organic structures and (ii) comparing digitized data about the patient's internal tissues with the stored data identifying a predetermined type of organic structure.

An endoscope system in accordance with the present invention aids an endoscopist in detecting and identifying polyps and other organic formations inside a patient. Inexperienced operators are provided essentially with the automated assistance of older, more experienced endoscopists, insofar as their prior experience may be recorded and stored in a memory accessible by an endoscope computer. Even the experienced endoscopist benefits from a diagnostic endoscope asystem in accordance with the invention. The effects on an endoscopic examination of momentary distractions originating outside the patient, as well as view-obstructing structural formations inside the patient, all of which might otherwise detract from the completeness of the examination, are obviated via automatic detection in accordance with the present invention.

DETAILED DESCRIPTION

Figure 1:
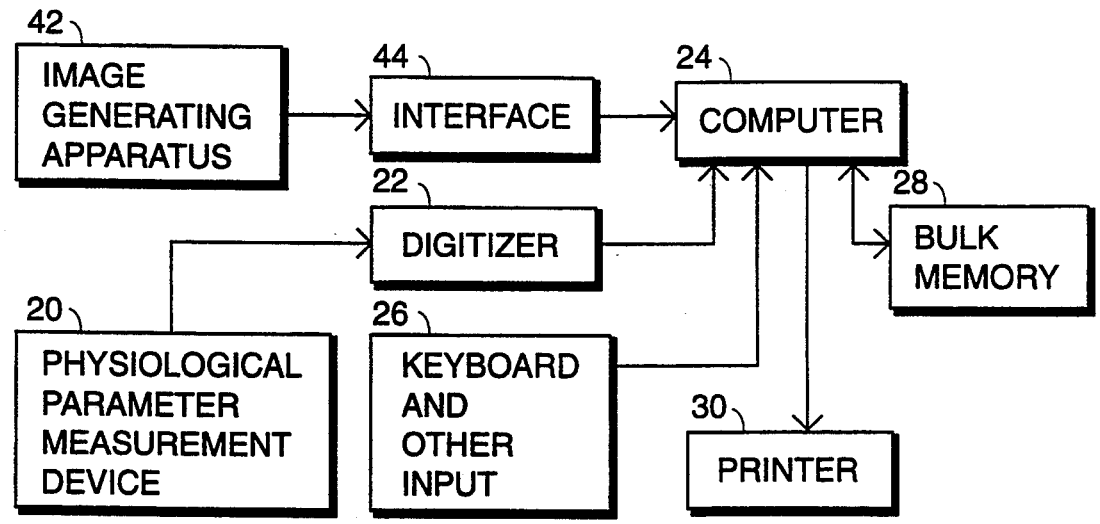
FIG. 1 is a block diagram of a medical diagnostic system utilizing principles in accordance with the present invention.

As illustrated in FIG. 1, a medical diagnostic system comprises a device 20 for monitoring and measuring a biological or physiological parameter. Monitoring and measuring device 20 is juxtaposable to a patient for collecting individualized medical data about the patient's condition. Device 20 may take the form of an electronic thermometer, an electronic blood pressure gauge, a pulmonary function apparatus, a doppler study apparatus, an EEG machine, an EKG machine, an EMG machine, or a pressure measurement device, etc., or include a plurality of such components.

Monitoring and measuring device 20 is connected at an output to a digitizer 22 which converts normally analog type signals into coded binary pulses and transmits the resulting digital measurement signal to a computer 24. Digitizer 22 may be incorporated into a housing (not shown) enclosing all or part of the monitoring and measuring device 20. Moreover, digitizer may be an integral part of monitoring and measuring device 20.

Computer 24 receives instructions and additional input from a keyboard 26. Keyboard 26 is used to feed computer 24 information for identifying the patient, for example, the patient's age, sex, weight, and known medical history and conditions. Such medical conditions may include past diseases and genetic predispositions.

Computer 24 is also connected to an external memory 28 and an output device 30 such as a printer or monitor. Memory 28 stores medical data for a multiplicity of previously diagnosed medical conditions which are detectable by analysis of data provided by monitoring and measuring device 20.

Figure 2:
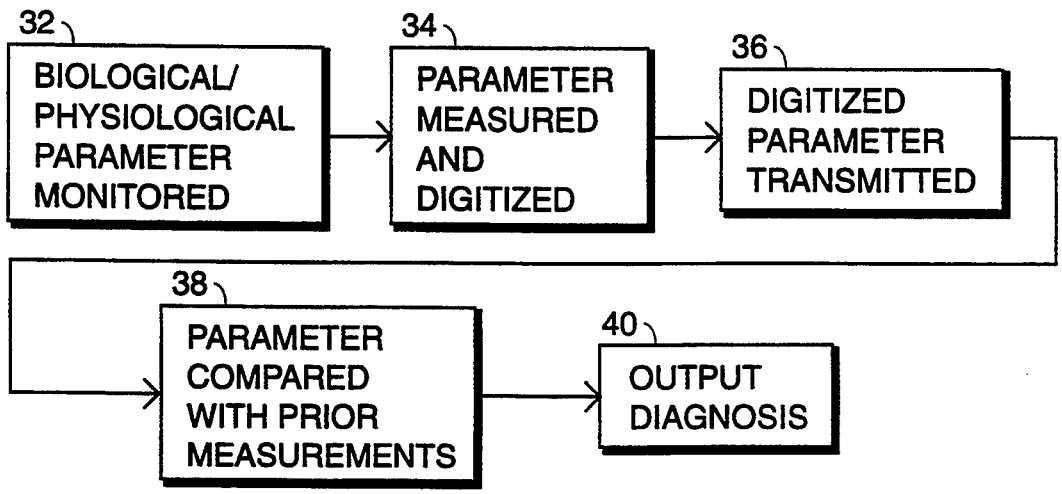
FIG. 2 is a flow-chart diagram illustrating steps in a mode of operation of the diagnostic system of FIG. 1.

As illustrated in FIG. 2, monitoring and measuring device 20 detects a magnitude of a predetermined biological or physiological parameter in a step 32. Digitizer 22 converts the detected magnitude into a pre-established digital format in a step 34 and transmits the digital signal to computer 24 in a step 36. Computer 24 is operated in a step 38 to compare the digitized data from monitoring and measuring device 20 with the data stored in memory 28 and to derive a diagnosis as to the patient's condition. The diagnosis is then communicated to the user (operator) and to the patient via output device 30 in a step 40.

If monitoring and measuring device 20 measures a physiological function characterized by a plurality of different variables, for example, the electric potential at different points on the patient's body (EEG, EKG, EMG), these variables may be broken down by computer 24 into one or more parameters, e.g., a frequency packet. The measured values of the pre-established parameters are then compared with parameter ranges stored in memory 28 for the type of parameter and the kind of patient, as characterized by sex, age, weight, etc. If the measured values of the pre-established parameters fall within expected ranges, as stored in memory 28, then computer 28 communicates a "normalcy" finding via printer 30. If, on the contrary, the measured values of one or more parameters fall outside the normal ranges, then a diagnosis of a possible medical condition is printed out.

As further illustrated in FIG. 1, the medical diagnostic system may comprise, in addition to or alternatively to monitoring and measuring device 20, an image generating apparatus or scanner 42 for generating in electrically encoded form a visually readable image of an organic part of the patient. Scanner 42 may take the form of an MRI apparatus, a CAT scanner, an X-ray machine, an ultrasonography apparatus, or a video camera with or without magnification optics for magnifying a sample on a slide. The video camera can be used for obtaining an image of a portion of a patient's skin.

Scanner 42 is connected via an interface 44 to computer 24.

Figure 3:
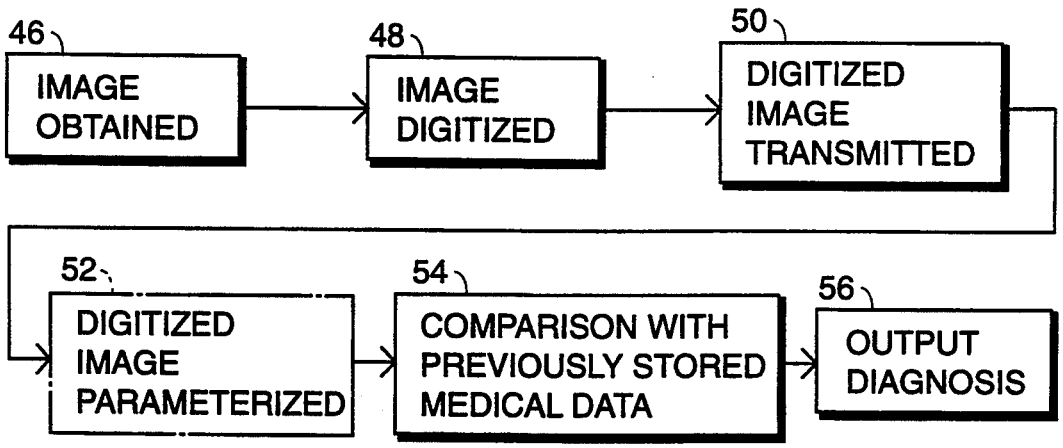
FIG. 3 is a flow-chart diagram illustrating steps in another mode of operation of the diagnostic system of FIG. 1.

As shown in FIG. 3, scanner 42 obtains an image of a tissue or organ in a step 46. The image is digitized, either by scanner 42 or interface 44 in a step 48, and is transmitted to computer 24 in a step 50. Computer 24 is operated in a step 52 to analyze the image from scanner 42 and determine specific values for a multiplicity of predetermined parameters. For example, in the event that scanner 42 takes the particular form of a video camera for dermatological diagnosis, an image of a skin surface of a patient is analyzed by computer 24 to derive such parameters as percentage of skin covered by abnormal condition, the range of sizes of individual ulcers, the range of color variation (e.g., whether bleeding is symptomatic).

The specific values of pre-established parameters calculated by computer 24 from electrically encoded images transmitted from scanner 42 are compared by computer 24 with previously determined parameter ranges stored in memory 28. For example, if a pregnant woman's fetus is being scanned by ultrasonography, the lengths of the fetal appendages, arms, legs, fingers, etc., are compared with each other and with respective fetal appendage ranges recorded in memory 28 for the stage of pregnancy, weight of the fetus, and possibly weight of the mother. In the event that any appendages are missing or are of abnormal length, a diagnosis as to possible deformity is printed out. Organs internal to the fetus may be similarly examined automatically by scanner 42 and computer 24. In more advanced stages of pregnancy, physiological functions such as the heart rate of the fetus may be automatically monitored for abnormal conditions.

The analysis performed by computer 24 on the image from scanner 42 will depend in part on the region of the patient's body being scanned. If a woman's breast or a person's cortex is being monitored for tumorous growths, computer 24 is programmed to separate the tissue image into regions of different textures. The different textured regions are parameterized as to size, shape and location and the derived parameters are compared to values in memory 30 to determine the presence of a tumor. Additional analysis is undertaken to detect lines in an image which may indicate the presence of an organic body.

A similar analysis is undertaken to evaluate a tissue specimen on a slide. The texture and line scanning may be repeated at different magnification levels if, for example, the tissue sample is a slice of an organ wall. On a high magnification level, the texture and line analysis can serve to detect microorganisms in blood.

Memory 28 may store entire images related to different diseases. For example, memory may store images of skin conditions in the event that scanner 42 takes the form of a video camera at a dermatological diagnosis and treatment facility. In a step 54 (FIG. 3), computer 24 compares the image of a patient's skin with previously stored images in memory 28, for example, by breaking down the current image into sections and overlaying the sections with sections of the stored images, at variable magnification levels.

In the event that scanner 42 takes the form of an MRI apparatus or CAT scanner, the images stored in memory 28 are of internal organic structures. In step 54 (FIG. 3), computer 24 compares images of a person's internal organs with previously stored organ images in memory 28. Computer 24 partitions the image from the MRI apparatus or CAT scanner into subareas and overlays the subareas with sections of the stored images, at variable magnification levels.

In a final step 40 (FIG. 3), computer 24 communicates the results of its diagnostic evaluation to a user or patient.

Figure 4:
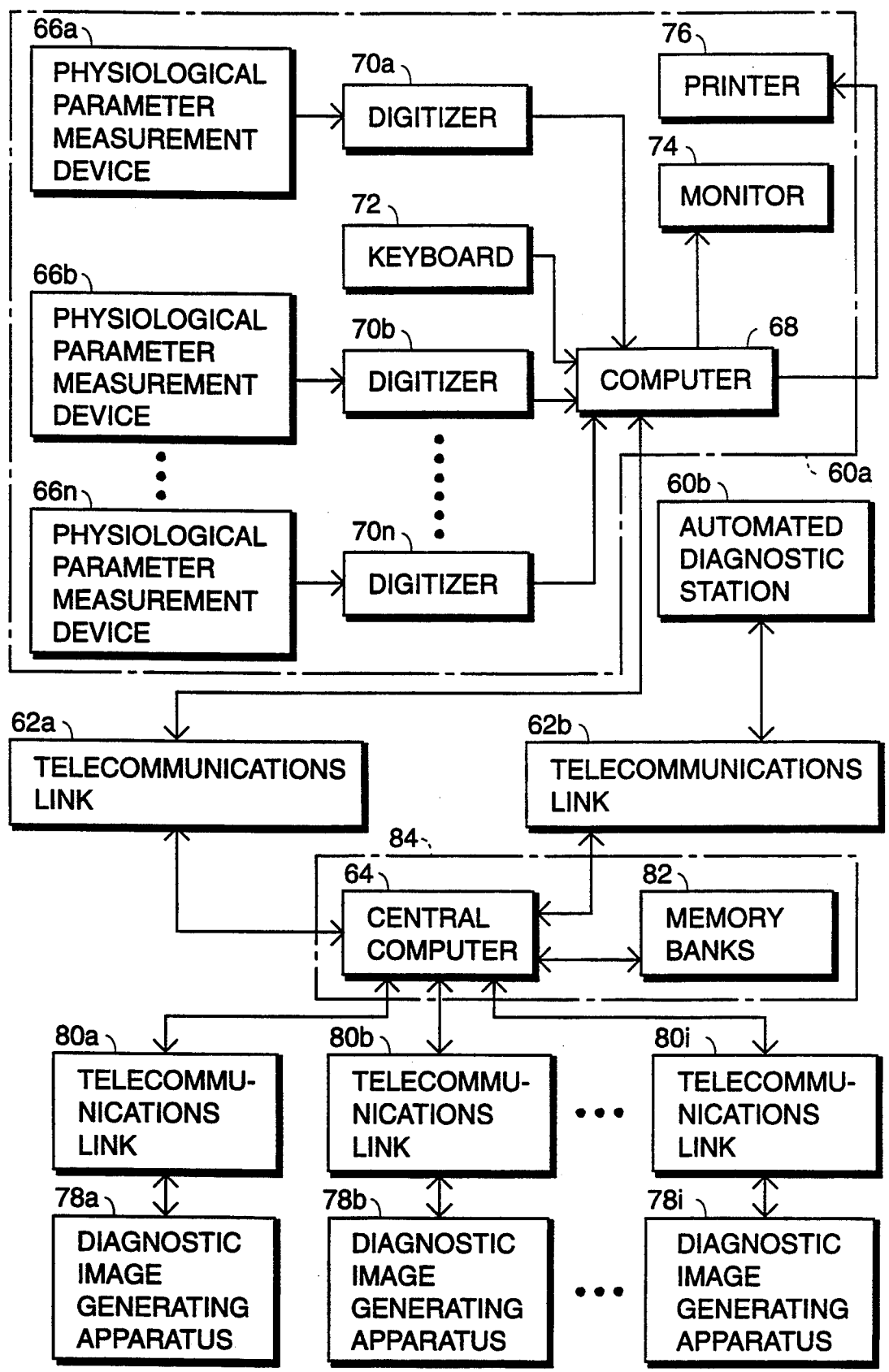
FIG. 4 a block diagram of a further medical diagnostic system in accordance with principles of the present invention.

As illustrated in FIG. 4, a medical diagnostic system comprises a plurality of remote automated diagnostic stations 60a and 60b connected via respective telecommunications links 62a and 62b to a central computer 64. Each diagnostic station 60a, 60b may take the form shown in FIG. 1, local computer 24 communicating via link 62a, 62b with central computer 64. Alternatively, each diagnostic station 60a, 60b may take the form shown in FIG. 4 and include a respective plurality of monitoring and measuring devices 66a, 66b, . . . 66n operatively connected to a local computer 68 via respective digitizer output units 70a, 70b, . . . 70n. Computer 68 is fed instructions and data from a keyboard 72 and communicates diagnostic results via a monitor 74 or printer 76. As discussed hereinabove with reference to monitoring and measuring device 20 of FIG. 1, each monitoring and measuring device 66a, 66b, . . . 66n is juxtaposable to a patient for collecting individualized medical data about the patient's condition. Monitoring and measuring devices 66a, 66b, . . . 66n may resepctively take the form of an electronic thermometer, an electronic blood pressure gauge, a pulmonary function apparatus, a doppler study apparatus, an EEG machine, an EKG machine, an EMG machine, or a pressure measurement device, etc.

Digitizers 70a, 70b, . . . 70n convert normally analog type signals into coded binary pulses and transmit the resulting digital measurement signals to computer 68. Digitizers 70a, 70b, . . . 70n may be incorporated into the housings or casing (not shown) enclosing all or part of the respective monitoring and measuring devices 66a, 66b, . . . 66n.

Keyboard 72 is used to feed computer 68 information for identifying the patient, for example, the patient's age, sex, weight, and known medical history and conditions. Such medical conditions may include past diseases and genetic predispositions.

As further illustrated in FIG. 4, a plurality of diagnostic image generating apparatuses or scanners 78a, 78b, . . . 78i are also connected to central computer 64 via respective telecommunications links 80a, 80b, . . . 80i. Scanners 78a, 78b, . . . 78i each generate in electrically encoded form a visually readable image of an organic part of the patient. Scanners 78a, 78b, . . . 78i may each take the form of an MRI apparatus, a CAT scanner, an X-ray machine, an ultrasonography apparatus, or a video camera with or without magnification optics for magnifying a sample on a slide.

Because of the enormous quantity of data necessary for storing images, central computer 64 is connected to a bank of memories 82 at a central storage and information processing facility 84. Diagnosis of patient conditions may be undertaken by central computer 64 alone or in cooperation with local computers 24 or 68.

Figure 5:
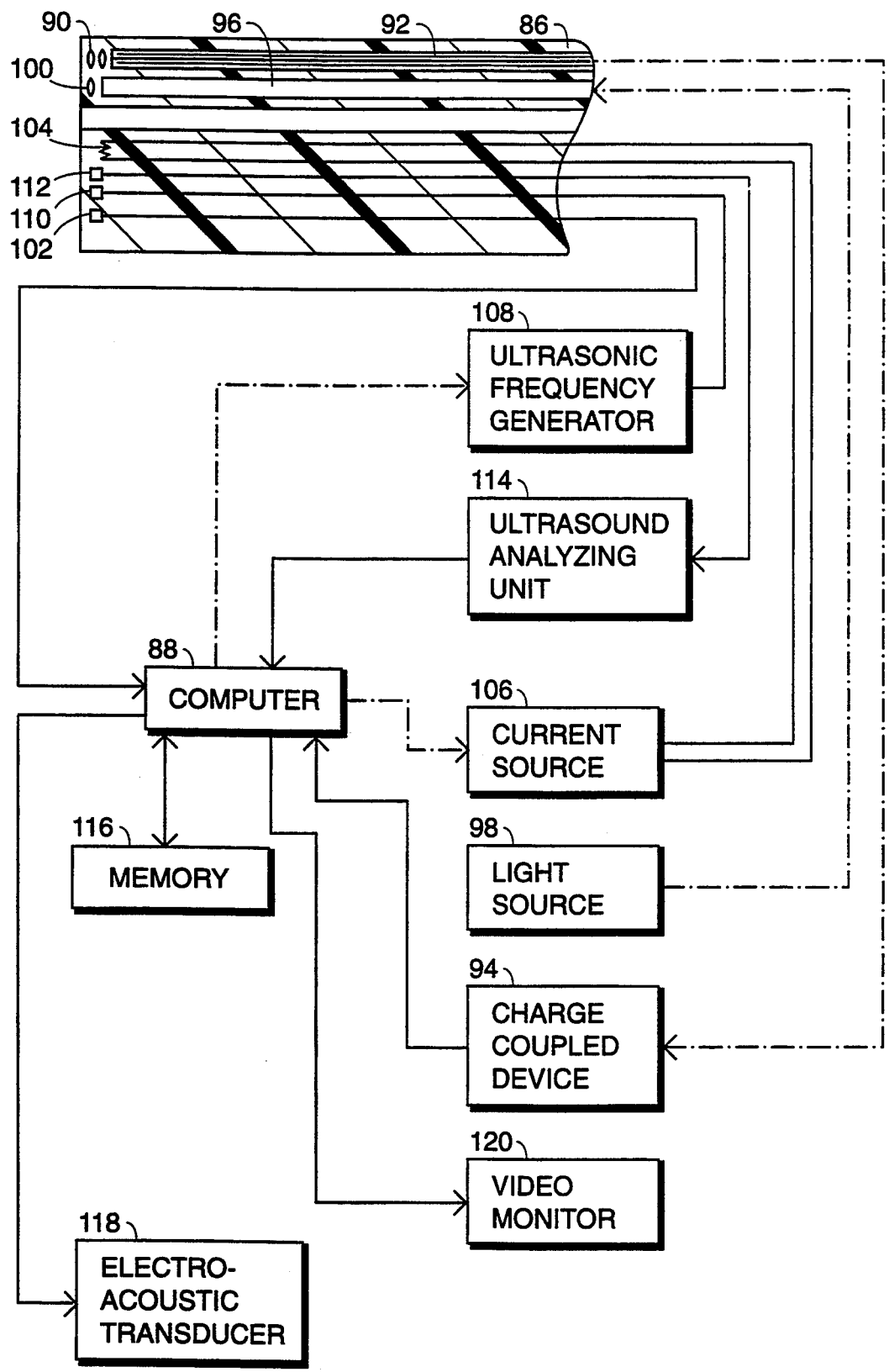
FIG. 5 is a partially a partial schematic longitudinal cross-sectional view of an endoscope insertion member and partially a block diagram of an endoscope system in accordance with the present invention.

As illustrated in FIG. 5, a system for use in medical diagnosis in the context of an endoscopic investigation or examination comprises an endoscope insertion member 86 and a computer 88 for automatically detecting polyps and other organic structures inside a patient. An optical frequency lens assembly 90 is mounted to the distal end of endoscope insertion member 86 for receiving and focusing onto a distal end of an optical fiber bundle 92 incoming optical wave energy reflected from internal body tissues. Bundle 90 extends to a video scanner in the form of a charge coupled device or CCD 94 which may be mounted directed to the endoscope.

Optical frequency electromagnetic radiation is transmitted from a light source 98 via an optical fiber 96 extending through insertion member 86. Optical fiber 96 terminates at a lens 100 at the distal tip of insertion member 86.

Infrared wave energy from internal body tissues of a patient is detected by an infrared sensor or scanner 102 (e.g., a charged coupled device) mounted to endoscope insertion member 86. Infrared sensor 102 is connected to computer 88 for providing that unit with electrical signals encoding infrared radiation emissions from internal organic tissues. The temperature of the tissues may be elevated by a heating element 104 disposed at the distal end of endoscope insertion member 86. Heating element is connected to a current source 106 which is operable under the control of computer 88.

An ultrasonic frequency generator 108 is operatively connected to an electroacoustic transducer 110 mounted to the endoscope insertion member 86 at the distal end thereof for producing ultrasonic pressure waves. In accordance with known principles, the ultrasonic waves are differentially reflected from internal body tissues to provide structural information as to the tissues. Reflected ultrasonic wave energy is detected by a sensor or scanner 112 disposed at the distal end of insertion member 86. Sensor or scanner 112 is operatively connected at an output to an ultrasound analyzer 114 in turn connected at an output to computer 88. Analyzer 114 provides computer 88 with digitized data encoding three dimensional structures of internal organs and tissues of a patient.

Similarly, sensor 102 provides computer 88 with digitized data encoding differential infrared emissions by the internal organ structures and tissues. The infrared emissions may be indicative of natural temperature gradients, susceptibility to heat produced by heating element 104, or absorbability of infrared emitting compositions administered to the patient. In the latter case, light source 98 may be designed to emit long wavelength radiation for inducing infrared fluorescence of intravenously injected tumor-specific markers. See U.S. Pat. No. 4,541,438 to Parker et al., the disclosure of which is hereby incorporated by reference.

Computer 88 is programmed to analyze incoming ultrasound data from analyzer 114, infrared data from sensor 102, and optical data from CCD 94 to determine the presence of predetermined types of organic structures of interest such as polyps. In executing its programming, computer 88 consults a memory 116 which stores previously collected data on such types of organic structures.

A signal generator in the form of an electroacoustic transducer or speaker 118 is operatively connected to computer 88 for automatically generating an audible alert signal sensible by an operator to inform the operator of the existence of a detected organic object of the predetermined type of types. In addition, computer 88 may be programmed to alter an image on a video monitor 120. Monitor 120 is connected to computer 88 for displaying images derived from incoming ultrasound data from analyzer 114, infrared data from sensor 102, and optical data from CCD 94. Upon determining the presence of a polyp or other object, computer 88 generates a circle or other highlighting artifact on the screen of monitor 120, thereby visually alerting the endoscopist as to the presence and location of the detected object. The circle encloses the image of the detected object on monitor 120. Other techniques of highlighting may include altering the brightness or color of the image of the detected object. Alternatively or additionally, computer 88 may be programmed for freezing an image on monitor 120 upon an identification of an object of a predetermined type.

The picture on monitor 120 may be subdivided to display a real time image of the tissues currently juxtaposed to the distal end of insertion member 86 and a frozen image incorporating the detected object. Accordingly, the endoscopist can return the distal tip of endoscope insertion member 86 to the location of a detected polyp after investigating a different area.

Upon the insertion of endoscope insertion member 86 into a patient, each of the endoscope's sensors, namely, infrared sensor 102, ultrasonic sensor 112, and optical frequency CCD 94 is operated to receive energy waves from internal body tissues of the patient proximate to a distal end of insertion member 86. Data from the energy waves is automatically digitized either by the respective sensor or by a downstream component such as analyzer 114 or an analog-to-digital component inside computer 88. The digitized data incorporates information as to internal organic structures of the patient.

Computer 88 automatically analyzes the incoming digitized data, from any one or all of sensors 102, 112 and 94, and automatically identifies an organic object of a predetermined type from the digitized data. It is known, for example, that polyps have charateristic shapes and textures, as well as a characterisic response to certain chemical compositions which are injected into the patient (U.S. Pat. No. 4,541,438). The data from sensors 102, 112 and 94 is compared with information stored in memory 116 and correlated by computer 88 to identify polyps and other possible objects of interest to the endoscopist.

On monitor 120, as discussed above, the alert signal may be implemented by highlighting an image of the organic object, for example, by generating a circle surrounding the image of the organic object on the monitor.

Although the invention has been described in terms of particular embodiments and applications, one of ordinary skill in the art, in light of this teaching, can generate additional embodiments and modifications without departing from the spirit of or exceeding the scope of the claimed invention. For example, a computer of an endoscope system in accordance with the present invention may be programmed not only to identify or detect polyps and other organic structures inside a patient but may also be programmed to identify and store the locations of the detected structures. Images of the identified structures may be stored for later presentation on a video monitor, for instance, to the patient. Alternatively or additionally, as described above, freeze-frame images of detected abnormal tissues may be displayed on a video monitor simultaneously with real time images of internal tissues. The different images may occupy respective windows on the monitor screen.

Accordingly, it is to be understood that the drawings and descriptions herein are proffered by way of example to facilitate comprehension of the invention and should not be construed to limit the scope thereof.

What is claimed is:

1. A medical method comprising the steps of:
providing an endoscope assembly including a flexible insertion member;
inserting said insertion member into a colon of a patient;
upon insertion of said insertion member into the patient's colon, generating visible light energy and emitting said light energy from a distal end of said insertion member;
collecting visible light energy reflected from organic tissues in the patient's colon upon said step of emitting;
transmitting, in a proximal direction along said insertion member, image information contained in the reflected light energy;
detecting, via said insertion member, infrared electromagnetic energy emitted by, said organic tissues;

in response to said step of detecting, generating an electrical signal;

transmitting said electrical signal in a proximal direction along said insertion member;

storing image type data for a multiplicity of previously identified internal organic structures;

operating a computer to compare said image information with said image type data and to analyze and correlate information contained in said electrical signal with said image information to automatically identify said organic tissues as a polyp; and automatically generating an alert signal sensible by an operator to inform said operator of the existence of the polyp.

2. The method defined in claim 1, further comprising the step, implemented upon insertion of said insertion member into the patient's colon, of generating heat energy at said distal end of said insertion member and elevating a temperature of said organic tissues prior to said step of detecting.

3. The method defined in claim 1, further comprising the steps of injecting a tumor specific marker composition prior to said step of detecting and emitting long-wavelength radiation from said distal end of said insertion member prior to said step of detecting and upon insertion of said insertion member into the colon of the patient.

4. The method defined in claim 1, further comprising the steps of:

generating ultrasonic pressure waves;

emitting said pressure waves from said insertion member towards said organic tissues;

detecting ultrasonic pressure waves reflected from said organic tissues;

analyzing the reflected ultrasonic pressure waves to produce digitized data encoding a three dimensional structure of said organic tissues;

operating said computer to analyze and correlate said digitized data with information contained in said electrical signal and with said image information to identify said organic tissues.

5. The method defined in claim 1, further comprising the step of displaying an image of said organic tissues, said step of generating an alert signal including the step of displaying a visual indicator in said image to highlight said organic tissues.

6. The method defined in claim 1 wherein said step of generating an alert signal includes the step of freezing an image of said organic tissues on a monitor.

7. A medical method comprising the steps of:

providing an endoscope assembly including a flexible insertion member;

inserting said insertion member into a colon of a patient;

upon insertion of said insertion member into the patient's colon, generating visible light energy and emitting said light energy from a distal end of said insertion member;

collecting light energy reflected from organic tissues in the patient's colon upon said step of emitting;

transmitting, in a proximal direction along said insertion member, image information contained in the reflected light energy;

generating ultrasonic pressure waves;

emitting said pressure waves from said insertion member towards said organic tissues;

detecting ultrasonic pressure waves reflected from said organic tissues;

analyzing the reflected ultrasonic pressure waves to produce digitized data encoding a three dimensional structure of said organic tissues;

storing image type data for a multiplicity of previously identified internal organic structures;

operating a computer to compare said image information with said image type data and to analyze and correlate said digitized data with said image information to automatically identify said organic tissues as a polyp; and automatically generating an alert signal sensible by an operator to inform said operator of the existence of the polyp.

8. The method defined in claim 7, further comprising the step of displaying an image of said organic tissues, said step of generating an alert signal including the step of displaying a visual indicator in said image to highlight said organic tissues.

9. The method defined in claim 7 wherein said step of generating an alert signal includes the step of freezing an image of said organic tissues on a monitor.

* * * * *